US009884016B2

(12) United States Patent
Huang

(10) Patent No.: US 9,884,016 B2
(45) Date of Patent: *Feb. 6, 2018

(54) STABLE PHARMACEUTICAL COMPOSITION OF CLOPIDOGREL FREE BASE FOR ORAL AND PARENTERAL DELIVERY

(71) Applicant: Jingjun Huang, Monmouth Junction, NJ (US)

(72) Inventor: Jingjun Huang, Monmouth Junction, NJ (US)

( * ) Notice: Subject to any disclaimer, the term of this patent is extended or adjusted under 35 U.S.C. 154(b) by 45 days.

This patent is subject to a terminal disclaimer.

(21) Appl. No.: 15/279,848

(22) Filed: Sep. 29, 2016

(65) Prior Publication Data

US 2017/0014343 A1    Jan. 19, 2017

Related U.S. Application Data

(63) Continuation of application No. 14/174,351, filed on Feb. 6, 2014, now Pat. No. 9,480,680.
(Continued)

(51) Int. Cl.
*A61K 9/14* (2006.01)
*A61K 31/44* (2006.01)
(Continued)

(52) U.S. Cl.
CPC ............ *A61K 9/107* (2013.01); *A61K 9/0019* (2013.01); *A61K 9/1075* (2013.01);
(Continued)

(58) Field of Classification Search
CPC .... C07D 495/04; A61K 9/4365; A61K 9/107; A61K 9/1075; A61K 47/10; A61K 47/02; A61K 47/44; A61K 47/24
See application file for complete search history.

(56) References Cited

U.S. PATENT DOCUMENTS 6,720,001 B2    4/2004  Chen et al.
9,480,680 B2 *  11/2016 Huang ............... A61K 31/4365
(Continued)

FOREIGN PATENT DOCUMENTS

CN    102697724 a   * 10/2012 ............. A61K 9/107
CN    102697724 A    10/2012
(Continued)

OTHER PUBLICATIONS

PCT Notification of Transmittal of International Search Report and Written Opinion, dated Jun. 10, 2014.
(Continued)

*Primary Examiner* — Lakshmi Channavajjala
(74) *Attorney, Agent, or Firm* — Gearhart Law LLC

(57) ABSTRACT

The present disclosure provides ready-to-use, oil/water emulsion compositions with mean droplet size (intensity-average, nm) of 100-500 nm, where the oil phase comprises clopidogrel free base dispersed in pharmaceutical acceptable oil(s). The emulsion uses clopidogrel free base or premix of clopidogrel free base in oil(s) as the starting materials and may also contain one or more excipients such as surfactant and or co-surfactant, osmotic agent, pH adjustment agent, antioxidant, preservative, sweetener, and/or suspending agent, etc.

18 Claims, 4 Drawing Sheets

Related U.S. Application Data

(60) Provisional application No. 61/761,234, filed on Feb. 6, 2013.

(51) Int. Cl.

| | | |
|---|---|---|
| *A61K 9/107* | (2006.01) | |
| *A61K 31/4365* | (2006.01) | |
| *A61K 47/10* | (2017.01) | |
| *A61K 47/14* | (2017.01) | |
| *A61K 47/44* | (2017.01) | |
| *A61K 9/00* | (2006.01) | |
| *A61K 47/02* | (2006.01) | |
| *A61K 47/24* | (2006.01) | |

(52) U.S. Cl.
CPC .......... *A61K 31/4365* (2013.01); *A61K 47/02* (2013.01); *A61K 47/10* (2013.01); *A61K 47/14* (2013.01); *A61K 47/24* (2013.01); *A61K 47/44* (2013.01)

(56) References Cited

U.S. PATENT DOCUMENTS

| | | |
|---|---|---|
| 2007/0003628 A1 | 1/2007 | Liversidge et al. |
| 2010/0062066 A1* | 3/2010 | Bernstein ............. A61K 9/1075 424/486 |

FOREIGN PATENT DOCUMENTS

| | | | |
|---|---|---|---|
| KR | 2007034681 A * | 3/2007 | ......... A61K 31/4365 |
| WO | 2008060934 A2 | 5/2008 | |
| WO | 2012122493 A1 | 9/2012 | |

OTHER PUBLICATIONS

PCT Notification of Transmittal of International Preliminary Report on Patentability, dated Aug. 20, 2015, pp. 8.

European Supplementary Search Report, dated Jun. 22, 2016.

* cited by examiner

STABLE PHARMACEUTICAL COMPOSITION OF CLOPIDOGREL FREE BASE FOR ORAL AND PARENTERAL DELIVERY

PRIORITY CLAIM

This application claims priority to U.S. application Ser. No. 14/174,351 filed on Feb. 6, 2014 which claims priority to U.S. Provisional Patent No. 61/761,234 filed on Feb. 6, 2013, the contents of both of which are hereby fully incorporated herein by reference in their entirety.

FIELD OF THE INVENTION

The present invention relates to oil/water emulsion compositions containing clopidogrel free base dispersed in oils that significantly improve the stability of clopidogrel against chiral, hydrolytic, and thermal degradations, and to the methods of making and using thereof in the treatment of mammal, particularly human subjects in need of clopidogrel.

BACKGROUND OF THE INVENTION

Clopidogrel, methyl (+)-(S)-α-(o-chlorophenyl)-6,7-dihydrothieno[3,2-c]pyridine-5(4H)-acetate, is an anticoagulant drug that inhibits platelet aggregation by selective binding to adenylate cyclase-coupled ADP receptors on the platelet surface. It is widely used for the prevention of atherothrombotic events such as myocardial infarction, stroke, peripheral arterial disease, acute coronary syndrome, and cardio-vascular death. The structure of the S-enantiomer of clopidogrel is shown below in structure (I):

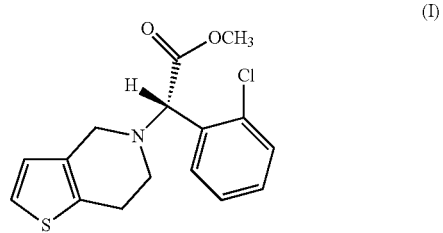 [SMILES: COC(=O)[C@H](c1ccccc1Cl)N1CCc2sccc2C1]

(I)

Clopidogrel (Such as Plavix® and other generics) is currently only available as a tablet form containing 75 mg equivalents of the clopidogrel base; the drug is present in the bisulfate salt form. There is no liquid injectable or liquid oral dosage form currently available in the market. PLAVIX® is an antiplatelet medication approved by the U.S. Food and Drug Administration to reduce thrombotic events and patients with acute coronary syndrome. For an average loading dose (300 mg clopidogrel in a PLA VIX® tablet), the typical time to reach the desired therapeutic effect (e.g. platelet aggregation inhibition) varies from two to five hours probably due to delay in absorption, delay in system availability, or suboptimal bioavailability. If there is an immediate need for the procedure (such as percutaneous coronary intervention (PCI) in less than two to three hours), a larger than average dose of clopidogrel is usually administered to patient in order to achieve faster onset, which could potential cause deadly side effects such as hemorrhage, and long bleeding.

Therefore, there is an urgent need for liquid clopidogrel dosage form that could be administered as injectable or oral solution to achieve rapid therapeutic effect without increasing the dose. The ability to formulate clopidogrel in a biocompatible vehicle having minimum side effects and appropriate pharmadynamic profiles is critical to the use of clopidogrel as an intravenous or oral liquid agent. This is particular challenge for clopidogrel because of its lipophilicity, pH-dependent solubility with very low solubility at physiological pH, and extremely chemical instability at alkaline pH.

Clopidogrel is a weakly base with pKa of 4.5. It is practically insoluble in water at neutral pH but freely soluble at pH 1. It also dissolves freely in methanol, dissolves sparingly in methylene chloride, and is practically insoluble in ethyl ether. It has a specific optical rotation of about +56°. Clopidogrel free base is a semi-solid, oily form with high-viscosity, which causes problems in storage or handling process. Moreover, it has been reported that clopidogrel free base was not suitable for use in pharmaceutical dosage forms, which is unstable under increased moisture and temperature. Due to a labile proton in the chiral center and the methyl ester group, it was very susceptible to racemization, oxidation, and hydrolysis of a methyl ester group. It was reported that antioxidants did not prevent this degradation, and higher pH accelerated instability. As a result, it was indicated that clopidogrel should only be stabilized with salt-forming acids before incorporated into dosage forms.

Clopidogrel bisulfate, which is currently used in the commercial oral tablet Plavix® (Sanofi Aventis), is one of the salt examples used in oral dosage form. It is supplied in tablet form containing 75 mg equivalents of the clopidogrel base. Similarly to free base, clopidogrel biosulfate is also relatively unstable under increased moisture and temperature and in alkaline pHs due to its susceptibility to racemization, oxidation, and hydrolysis of a methyl ester group. Clopidogrel is a chiral molecule and can therefore exist as an R or an S enantiomer. The S-enantiomer is biologically active, while the R-enantiomer (impurity C) does not exhibit any anti-aggregation activity and is poorly tolerated. It can evoke convulsions at high doses of animals. The major circulating compound after administration is the inactive carboxylic acid derivative, which is formed by hydrolysis of the ester function by carboxylesterase. Carboxylic acid derivative (S)-(+)-(2-chlorophenyl)-6,7-dihydro-4H-thieno[3,2-c]pyridine-5-yl acetic acid (clopidogrel acid, Impurity A), which can be obtained by the hydrolysis of the ester group, either in vitro, catalyzed by the increased humidity, pH, and temperature, or in vivo, as a result of the action of enzyme carboxylesterase, is the main degradation product having no pharmacological activity. This implies that the content of the R-enantiomer as well as the inactive carboxylic acid derivative must be carefully controlled in clopidogrel bulk substance and drug products. The structure of those impurities listed in USP 32 and EP are shown below:

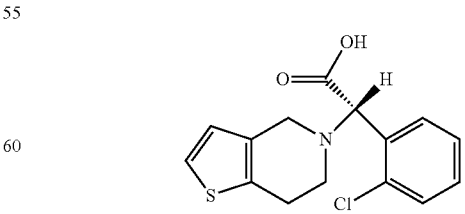

Imp. C1 (SR 26334)
(acid derivative)
Ph. Eur.: Impurity A
USP: Related compound A -continued

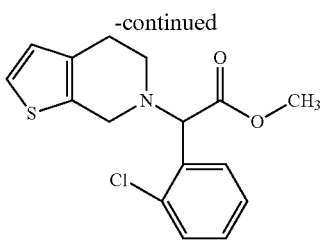

Imp. C2 (SR 24726)
(regio-isomer)
Ph. Eur.: Impurity B
USP: Related compound B

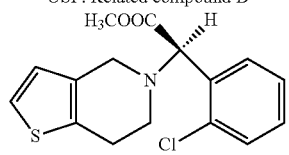

Imp. C3 (SR 25989)
(enantiomer)
Ph. Eur.: Impurity C
USP: Related compound C

The low solubility of clopidogrel in water at neutral pH makes it very difficult to develop a bioavailable and physical stable pharmaceutical product, particularly when intravenous or oral solutions are needed. Whereas its highly pH-dependent solubility make it very challenging to make a suitable aqueous-based injectable dosage forms that will not precipitate out when contact with body fluid and will not cause injection pain, phlebitis, and even embolism upon administration. Moreover, chemical instability of clopidogrel, in the presence of moisture, heat, and alkaline pH, precludes the use of aqueous solvent in the formulation, limits its formulation to organic solvent-based liquid or freeze-dried solid, and restrict its storage condition to a low storage temperature such as refrigeration or freezing.

A number of approaches for preparing intravenous and oral liquid compositions of sparingly or poorly water-soluble basic drugs are available. These methods include micellar solubilization or drug nanoparticle suspension by means of surface-active agents; formation of complexes with cyclodextrin and its derivatives (Hydroxypropyl beta-Cyclodextrin (HPBCD) and sulfobutylether-β-cyclodextrin (SBECD)); use of various co-solvent systems; and formation of salt with strong acid with a low solution pH. However, for micellar system, surfactants have been implicated by adverse effects such as hemolysis and histamine reaction and severe anaphylaxis reaction, and for nanosuspension system wherein pure drug particles of nanosize stabilized by polymer and surfactants, potential catalytic degradation of drug substance due to higher exposure area to aqueous media and the surrounding surfactants has been reported; taste masking and injection pain is another issue for the micellar/nanosuspension system due to a higher concentration of free drug available in the aqueous medium; co-solvent systems is known for causing precipitation, injection pain and phlebitis; potential nephrotoxicity and bradycardia and reduction of blood pressure caused by cyclodextrine and its derivatives and the potential concerns of cyclodextrin binding with coadministered lipophilic drugs have been reported; and the low solution pH of weakly basic salt formed with strong acid such as clopidogrel bisulfate will cause drug-excipient and product stability issue and cause tasting issue (clopidogrel has a bittering taste), injection site irritation and pain as a result of precipitation of the drug as free base when contact with blood at neutral pH. In summary, each of these methods listed above has its inherent limitations and are insufficient to formulate clopidogrel in a biocompatible vehicle having sufficient stability, minimum side effects, and appropriate pharmadynamic profiles as a either intravenous agent or oral solution agent.

WO 2008/060934 discloses an emulsion composition containing micronized oil droplets of pure tetrahydropyridine anti platelet agent stabilized by surfactant. Even though the publication mentions that the agent could be clopidogrel, the publication only discloses emulsion compositions using clopidogrel bisulfite as the starting material. Emulsion composition using clopidogrel free base as a starting material was not disclosed in the publication, and effects of drug form (free base or salt form) on the product stability, particularly on the drug-related impurity profiles of clopidogrel was not disclosed for the composition either.

CN102697724 discloses oil in water emulsion made with clopidogrel bisulfate or amino acid salts as the starting materials. However, the publication does not disclose emulsion compositions using clopidogrel free base as the starting material and the concentration of clopidogrel free base achieved in the emulsion composition is low (≤0.15% w/v), which may require a large volume of emulsion to achieve the required dose of 300 mg, In addition effects of drug form (free base or salt form) on the product stability, particularly on the drug-related impurity profiles of clopidogrel was not disclosed for the compositions either

SUMMARY OF THE INVENTION

To address the above mentioned flaws and problems in the current art, there is a need in the art for a clopidogrel liquid dosage form, particularly injectable, which is stable and ready-to-use, and can provide a single IV infusion containing up to 300 mg of clopidogrel dose for rapid therapeutic action, and can be prepared and stored at room temperature or refrigerated temperature. This disclosure provides such compositions. The compositions can be provided as antiplatelet agent for patient under emergence and intense care or who cannot take oral tablet administration, with such stability and purity to meet the requirements of the applicable compendium, Food and Drug Administration and GMP for use in preparation of a pharmaceutical formulation.

Considering the aforementioned problems, the present disclosure provides a surprising result that ready-to-use, aqueous-based oil/water parenteral or oral emulsion compositions containing clopidogrel free base with mean droplet size (intensity-average, nm) of 100-500 nm, wherein the oil phase comprises the clopidogrel free base dispersed in oils within acceptable limit of a surfactant and/or a co-surfactant, unexpectedly gives extremely favorable product stability and favorable impurity profiles at the time of exposure to high pH of ~9-10, or high pressure sterilization by water or steam, or after a long term storage, and thus superior quality and efficacy.

The present invention describes methods of controlling the amount of such impurities in a pharmaceutical compositions having clopidogrel as an active ingredient that meet USP 32 impurity specification for clopidogrel tablet. The emulsion formulations significantly improved the stability of clopidogrel over other aqueous based formulations (such as cyclodextrin-based formulations) or emulsion made with clopidogrel salt (such as bisulfate salt) with respect to chiral, hydrolysis, and thermal degradations.

1. One aspect of this invention is that the aqueous-based emulsion of this invention significantly reduced the hydrolysis of the methyl ester group (impurity A); Even though clopidogrel itself is very unstable at alkaline pH, the emulsion formulation prepared with pH adjusted to high pH at ~9-10 surprisingly show minimum amount of hydrolysis (<1.2%) over the shelf life, whereas unformulated clopidogrel degraded completely in 5 minutes in diluted NaOH solution under the same condition.

2. Another aspect of the invention is that the emulsion formulation of this invention surprisingly prevented thermal degradation of clopidogrel. It was known from literature that clopidogrel is unstable due to a labile proton in the chiral center and was susceptible to oxidation and even antioxidants did not prevent this degradation. To the contrary of the literature, the emulsion formulation of this invention inhibit the thermal degradation of clopidogrel without the use of antioxidant.

3. Another aspect of the invention is that the emulsion of this invention surprisingly inhibit chiral conversion of clopidogrel from the S-enantiomer (biologically active) to the R-enantiomer (which does not exhibit any anti-aggregation activity and is poorly tolerated) (impurity C<1.5%). This is contrary to the cyclodextrin-based solution formulation or emulsion formulation using clopidogrel salt (such as bisulfate salt) as the starting materials wherein significant amount of R-enantiomer was formed during process and storage.

4. Another aspect of the present invention describes pharmaceutical compositions prepared or stored using the manufacturing process methods described herein wherein the level of certain drug-related impurities is minimized or reduced.
   a) In particular, the present invention describes pharmaceutical composition having clopidogrel as an active ingredient, and having a reduced level of impurities that meet requirement of USP 32 impurity specifications for clopidogrel tablet.
   b) More specifically, the present invention describes a pharmaceutical composition having clopidogrel as an active ingredient, wherein the compositions contains equal or no more than 1.2% of clopidogrel related compound A, not more than 1.5% of clopidogrel related compound C, not more than 0.2% of any other single drug-related impurity (excluding clopidogrel related compound B), and not more than 2.5% of total impurities (excluding clopidogrel related compound B).

5. Another aspect of the present invention is a method of treating or alleviating a disease or condition in a subject in need thereof, comprising administering to the subject an effective amount of a pharmaceutical composition having clopidogrel free base as the active ingredient, wherein the level of impurities is reduced or minimized to no more than 2.5% total drug related impurity to clopidogrel (excluding clopidogrel related compound B). As used herein the disease or condition refers to any disease or condition which may be treated using clopidogrel containing medicine for the prevention of atherothrombotic events such as myocardial infarction, stroke, peripheral arterial disease, acute coronary syndrome, and cardio-vascular death.

It is an object of this invention to provide a stable pharmaceutical oil/water emulsion composition with nanosized oil droplets for parenteral or oral administration comprising: clopidogrel free base dispersed in an oil phase; a surfactant and an optional a co-surfactant; a water phase substantially free of clopidogrel; and a pH adjusting agent.

It is another object of this invention to provide a method to make a stable pharmaceutical oil/water emulsion composition with nanosized oil droplets for parenteral or oral administration, said method comprising the steps of: a) preparing an oil phase comprising clopidogrel by dispersing clopidogrel free base in an oil carrier; b) preparing an aqueous phase comprising water and a pH adjustment agent; c) incorporating a surfactant or optionally a co-surfactant in the oil phase or in the aqueous phase; d) dispersing the oil phase in the aqueous phase to form a coarse emulsion and adjusting pH to about 9; e) forming a final emulsion by sonicating or high pressure homogenizing the emulsion of step d), and adjusting pH to between 5.5 and 10; f) filtrating the final emulsion; and g) controlling product bioburden or sterility by aseptic process or terminal sterilization.

It is yet another object of this invention to a method to treat a patient in need of a single highdose of clopidogrel, said method comprising: a) providing in a liquid form of a pharmaceutical oil/water emulsion composition prepared by dispersing clopidogrel free base in an oil carrier; preparing an aqueous phase comprising water and an pH adjustment agent; dispersing the oil phase into the aqueous phase by sonicating or homogenizing to form nanosized oil droplets; and b) administering orally or parenterally a single dose of the composition, wherein the single dose contains up to 300 mg of clopidogrel free base.

DETAILED DESCRIPTION OF THE INVENTION

Figure 1:
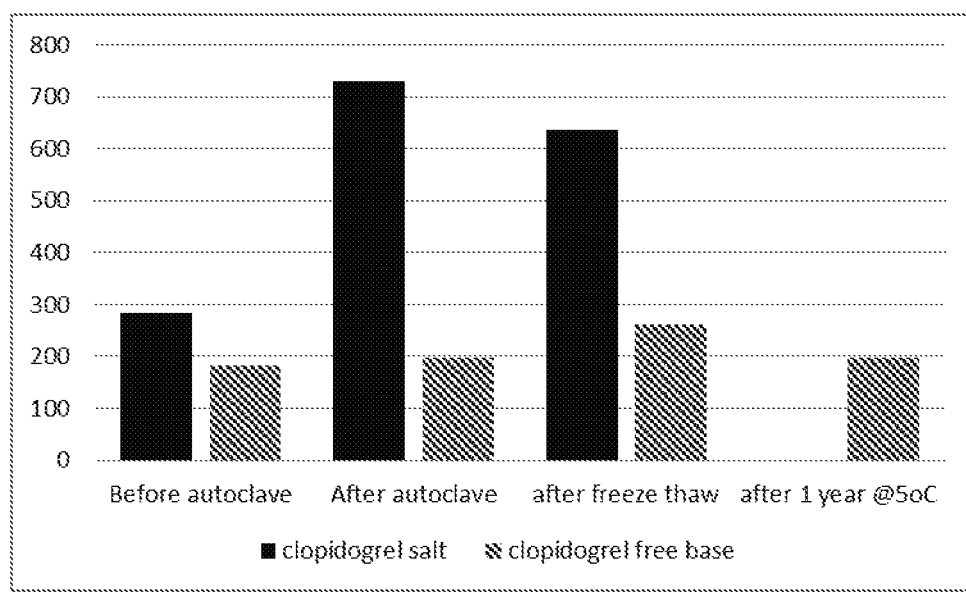
FIG. 1 shows the mean droplet size (intensity-average, nm) of the emulsions prepared with clopidogrel free base (Example 10) and clopidogrel bisulfate (Example 8) after autoclave and freeze-thaw conditions and storage under refrigeration (at ~5° C.) for 1 year.

The term "Clopidogrel drug substance" or "clopidogrel free base" is defined as: [methyl (+)-(S)-α-(o-chlorophenyl)-6,7-dihydrothieno[3,2-c]pyridine-5(4H)-acetate].

The term "clopidogrel related compound A" or "Impurity A" is defined as: [(+)-(S)-(o-chlorophenyl)-6,7-dihydrothieno[3,2-c]pyridine-5(4H)-acetic acid].

The term "clopidogrel related compound B" or "Impurity B" is defined as: [methyl (±)-(o-chlorophenyl)-4,5-dihydrothieno[2,3-c]pyridine-6(7H)-acetate].

The term "clopidogrel related compound C" or "Impurity C" is defined as: [methyl( )-(R)-(o-chlorophenyl)-6,7-dihydrothieno[3,2-c]pyridine-5(4H)-acetate].

The invention provides aqueous-based oil in water emulsion formulation composition with mean droplet size (intensity-average, nm) of 100-500 nm, comprising clopidogrel free base dispersed in oil(s) and a surfactant and/or a co-surfactant, and an aqueous liquid carrier. The formulation of the composition of this invention:
a) clopidogrel free base,
b) an oil phase,
c) a surfactant, and/or a co-surfactant, and
d) water and pH adjustment agent.

Optionally, the emulsion formulation may also contain chelate agent, antioxidant, osmotic agent, preservative, and buffering agent.

In some embodiments, the formulation further comprises a solubilizing agent, a flavoring agent, a sweetening agent, a viscosity inducing agent, electrolyte, another therapeutic agent, or a combination thereof.

Combinations of the various upper and lower limits to clopidogrel and other composition, as set forth in this disclosure, can be used to provide different embodiments of the invention. The invention also provides a method of administering clopidogrel comprising administering a ready-to-use liquid dosage formulation comprising clopidogrel free base dissolved in oil phase and aqueous phase thereof.

Emulsions of the invention offer much better stability and/or less side effects than other organic based or aqueous based dosage forms such as cyclodextrin-based formulation. Oil-in-water emulsions also prevent the lipophilic clopidogrel from adherence to the plastic infusion sets etc. during administration. The present invention also provides an emulsion of clopidogrel that is pharmaceutically stable at room temperature or refrigerated temperature and that does not require dilution prior to administration. Moreover, the emulsions give a fast release, together with faster therapeutic effect than conventional oral tablet dosage forms.

In some embodiments, the formulation does not require dilution prior to administration to a subject. In other embodiments; the liquid formulation may be diluted without precipitation of the clopidogrel. The formulation of the invention can be a single-dose or multi-dose formulation.

Some embodiments of the methods of the invention include those wherein the liquid formulation is administered by intravenous, oral, or enteric route. The present invention also provides a method of treating, preventing or reducing the occurrence of a disease associated with platelet aggregation or of a disease that requires clopidogrel therapy, the method comprising administering the formulation of the invention to a subject in need thereof. The invention also provides a method of decreasing the time to therapeutic onset or the time required to reach the target therapeutic effect provided by clopidogrel, comprising administering by parenteral, enteric, or oral route to a subject in need thereof, a formulation according to the invention. The formulation of the invention could provide a reduced time to therapeutic onset and/or to target therapeutic effect as compared to an oral solid tablet dosage form. The formulation of the invention also permits administration of a lower dose of clopidogrel to achieve a target therapeutic effect, e.g. target bleeding time or target inhibition of platelet aggregation, as compared to administration of a reference solid tablet oral dosage form to achieve the same target therapeutic effect.

According to one embodiment of this invention the emulsion comprises:
a) 0.01-10% w/w of clopidogrel free base;
b) 1-30% w/w of oil phase;
c) surfactant of 0.5-5.4% w/w;
d) co-surfactant of 0-0.5% (optional); and
d) 60-99% w/w of water and pH adjustment agent, such as sodium hydroxide to adjust pH above 5.

The Clopidogrel free base used for the formulation is a chiral molecule and can therefore exist as S-enantiomer. The S-enantiomer is biologically active, while the R-enantiomer (impurity C) does not exhibit any anti-aggregation activity and is poorly tolerated.

According USP 32, the active pharmaceutical ingredient used in the commercial tablet product, i.e. clopidogrel biosulfate is mainly S-enantiomer, i.e. not more than 0.2% of clopidogrel related compound A not more than 0.3% of the first enantiomer of clopidogrel related compound B; not more than 1.0% of clopidogrel related compound C; not more than 0.1% of any other drug-related impurity is found; and not more than 1.5% of total drug-related impurities.

As for the finished product after preparation and during storage, the commercial tablet product contains not more than 1.2% of clopidogrel related compound A, not more than 1.5% of clopidogrel related compound C, not more than 0.2% of any other single drug-related impurity (excluding clopidogrel related compound B), and not more than 2.5% of total drug-related impurities (excluding clopidogrel related compound B) according to USP32.

It has been generally recognized that clopidogrel free base was not suitable for use in pharmaceutical dosage forms due to its instability under increased moisture and temperature and susceptibility to racemization, oxidation, and hydrolysis of its methyl ester group, and that clopidogrel should only be stabilized with salt-forming acids before incorporated in to dosage forms. In this invention, use of clopidogrel free base is preferred over clopidogrel salt. Due to low solubility of clopidogrel salt in pharmaceutical-acceptable oil(s), its partition between oil and aqueous phase is low. As a result, the drug encapsulation efficient of clopidogrel dissolved in the oil phase (drug loading in oil phase) is low for clopidogrel salt. Therefore, formulation using clopidogrel salt as the drug substance will not be suitable to make emulsion containing a high drug loading (>0.15% clopidogrel free base drug load) when administration of clopidogrel dosage form as a single dose in a reasonable dose volume (such as 300 mg in 100 ml or less) is desired, unless very high level of surfactants or solvent are used. Otherwise, clopidogrel may crash out of the oil phase, dissolve, or precipitate into the aqueous phase, which will cause product homogeneity problem (presence of two forms, one is clopidogrel dissolved in oil, the other is free clopidogrel suspended in aqueous medium), stability problems as a result of clopidogrel exposed directly to water and ions that catalyze the degradation reaction, and injection site irritation/pain for injection and taste masking issue for oral dosage, and physical instability (precipitation) upon IV administration. In one embodiment of this invention, clopidogrel free base is used as is obtained from suppliers; in another embodiment, a composite containing the free base dissolved in pharmaceutical acceptable oil(s) is used as the starting materials for formulation. In another embodiment, clopidogrel free base is obtained by conversion of a clopidogrel salt to free base and separation of the counter ion from the free base prior to manufacturing.

The preferred range of clopidogrel free base in the formulation is 0.15-10%. The most preferred range of clopidogrel free base in the formulation is 0.2-3%.

Oil phases in the emulsion are any pharmaceutical-grade oil, preferably triglycerides such as, but not limited to soy bean oil, safflower seed oil, olive oil, cottonseed oil, sunflower oil, fish oil (containing the omega-3 fatty acids eicosapentaenoic acid (EPA), and docosahexaenoic acid (DHA)), castor oil, sesame oil, peanut oil, corn oil, and medium chain triglycerides (such as Miglyol 812 or 810). The oil phase may also contain surfactant and/or co-surfactant such as egg lecithin, soy lecithin, and other phosphorus lipids, propylene glycol diesters, oleic acid, or monoglycerides (such as acetylareal monoglycerides). The oil phase can also be a mixture of said ingredients.

The preferred lipid phase is soy bean oil, medium chain triglycerides (MCT), olive oil, and fish oil, either alone or mixture with others.

The most preferred oil phase is soy bean oil. The preferred range of oil carrier is 5-30%. The most preferred rang of oil carrier is 10-20%.

Surfactants are any pharmaceutically acceptable surfactant, preferably phospholipids extracted from egg yolk or soy bean, synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soy). Surfactants may also be non-ionic surfactants such as poloxamers (for example Poloxamer 188 and 407), poloxamines, polyoxyethylene stearates, polyoxyethylene sorbitan fatty acid esters or sorbitan fatty acid esters. Ionic surfactants may also be used such as cholic acid and deoxycholic acid or surface active deriviatives or salts thereof.

The most preferred surfactant is egg lecithin. The preferred range of surfactant is 0.6-2.4%. The most preferred range of surfactant is 1.2-1.8%.

The co-surfactant is selected from the group consisting of oleic acid, sodium oleate, cholic acid, sodium cholate, deoxycholic acid, deoxysodium cholate and a mixture thereof; wherein the said co-surfactant is presented in the said invention in the range of 0-0.5 w/v % of the composition.

The preferred range of water of buffer is 70-90%.

The emulsion may also contain co-solvents or other solubility enhancers, chelate agent, preservative, antioxidants, stabilizers, pH-adjusting agents or tonicity modifying agents, such as glycerol, polymer as suspending agent, and sweetener, etc.

Desirable emulsions are stable systems of intensity-average droplet size of 100-1000 nanometer with white to off-white color. The preferred intensity-average droplet size is 100-500 nanometer; the most preferred intensity-average droplet size is 100-300 nanometer.

The preferred pH range of the emulsion after manufacturing and during storage is 5.5 and above. In one embodiment, the pH of the emulsion is controlled to the range to 5.5-7; in another embodiment, the pH of the emulsion was controlled to 7-10. The preferred pH range of the emulsion is 6.5-9. The pH adjustment agent can be a buffer or sodium hydroxide or other pH adjustment agents or combine thereof.

The emulsion of the invention can be prepared in the following method: For the aqueous phase, pharmaceutical-grade water is dispensed to a container and heated to about 40-80° C. Egg lecithin and glycerin is added and pH is adjusted to 9-10. For the oil phase, soybean oil is dispensed into another container and heated to about 40-80° C. Clopidogrel and optionally co-surfactant is then added to the soybean oil and heated to about 40° C. to about 80° C. Optionally, egg lecithin can be added to the oil phase. The aqueous and oil phases are then mixed together by a high shear mixer to form a coarse emulsion. The emulsion is then sonicated or homogenized with a high pressure homogenizer or a micro-fluidizer at a pressure of about 5000-15000 psi and a temperature range of about 5° C. to about 60° C. to obtain an emulsion with a desired droplet size. The pH is adjusted with pH adjustment agent such as 1 N sodium hydroxide solution to a pH of about 5.5 to 10. In one embodiment, pH is adjusted to 9-10. In another embodiment, pH is adjusted to 7-10. In another embodiment, pH is adjusted to 8-10. The samples are filtered and dispensed into cleaned bottles, often with nitrogen gas overlay, and capped with siliconized rubber stoppers, and crimp sealed with an aluminum seal. The product can be manufactured by an aseptic process or by terminal sterilization. Preferably the dosage units are autoclaved to get sterile and stable emulsions. In one embodiment, the emulsion was autoclaved at 121° C. for 15-20 minutes. In another embodiment, the emulsion is processed aseptically under sterile environment without autoclave.

The invention is now described by way of non limiting examples. The invention comprises combinations of the embodiments and aspects of the invention as detailed herein. Accordingly, the invention also includes combinations and sub-combinations of the individual elements of the embodiments or aspects of the invention as described herein. Other features, advantages and embodiments of the invention will become apparent to those skilled in the art by the following description, accompanying examples. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention. A skilled artisan would realize that various changes and modifications may be made without diverting from the spirit of the invention.

Example 1. Comparison of Drug Partition Between Oil and Aqueous Phase for Clopidogrel Bisulfate and Free Base In order to determine percentage of clopidogrel partitioning in oil and aqueous phases, a partition study was conducted using clopidogrel biosulfate and clopidogrel free base. 600 mg of drug was weighed out and added to a beak containing equal weight of soy bean oil and DI water (20 g each). Stir the mixture in room temperature for 24 hours. At the end of study, samples from both phases were withdrawn and tested by HPLC as described in Example 14. The pH of the aqueous phase were measured.

Table 1 shows that that there could be about 50% of clopidogrel staying in the aqueous phase when clopidogrel bisulfate is used for the study. To the contrary, the amount of clopidogrel in the aqueous phase is negligible when free base is used for the partition study. This study suggests that if we would like to minimize amount of free clopidogrel in the aqueous phase, the free base will be preferred over its bisulfate salt. Otherwise, there could have formulation inhomogeneity and stability problems.

TABLE 1

Oil/water partition study

| Phase | Concentration (mg/mL) Bisulfate salt | mg/mL Free base |
|---|---|---|
| Oil Phase | 17 | 29 |
| Aqueous Phase | 15 | 0.006 |
| O/W partition ratio | 1.1 | 4833 |
| pH of aqueous phase | 2 | 7 |

Example 2. Preparation of Emulsion Using Clopidogrel Free Base Obtained as is from the Supplier

| Formula | Quantities: g |
|---|---|
| Clopidogrel free base | 0.20 |
| soy bean oil | 10.0 |
| egg lecithin | 1.2 |
| glycerol | 2.25 |
| sodium hydroxide | q.s. to pH 9-10 |
| Water for Injections | to 100 g |

All processing stages are carried out under nitrogen.

A sterile aqueous oil-in-water emulsion for parenteral administration is prepared as follows:

1. An aqueous phase is prepared from glycerol, and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, clopidogrel free base and egg lecithin, in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 9-10.
6. The mixture is then sonicated with an ultrasonic processor (Fisher Scientific Sonic Dismembrator, Model 500) with for 30 minutes. The product temperature is controlled at ~45 degree C.
7. The resultant oil-in-water emulsion is cooled, pH adjust to 9-10 if necessary, and then transferred into a filling vessel.
8. The emulsion is then filtered with 0.45 micron filter and filled into containers under nitrogen and autoclaved at 121 C for 20 minutes.
9. The final pH is ~8.

Example 3. Preparation of Emulsion Using Clopidogrel Free Base Obtained as is from the Supplier

| Formula | Quantities: g |
|---|---|
| Clopidogrel free base | 0.6 |
| soy bean oil | 10.0 |
| egg lecithin | 1.8 |
| glycerol | 2.25 |
| sodium hydroxide | q.s. to pH 9-10 |
| Water for Injections | to 100 g |

All processing stages are carried out under nitrogen.

A sterile aqueous oil-in-water emulsion for parenteral administration is prepared as follows:

1. An aqueous phase is prepared from glycerol, lecithin and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, and clopidogrel free base in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 9-10.
6. The mixture is then homogenized with a high pressure homogenizer (APV 2000) at ~10,000 psi for 10 cycles. The product temperature is controlled at ~45 degree C.
7. The resultant oil-in-water emulsion is cooled, pH adjust to 9-10 if necessary, and then transferred into a filling vessel.
8. The emulsion is then filtered with 0.45 micron filter and filled into containers under nitrogen and autoclaved at 121 C for 20 minutes.
9. The final pH is ~8.

Example 4. Preparation of Emulsion Using Clopidogrel Free Base Obtained as is from the Supplier

| Formula | Quantities: g |
|---|---|
| Clopidogrel free base | 3.0 |
| soy bean oil | 10.0 |
| egg lecithin | 1.2 |
| glycerol | 2.25 |
| sodium hydroxide | q.s. to pH 9-10 |
| Water for Injections | to 100 g |

All processing stages are carried out under nitrogen.

A sterile aqueous oil-in-water emulsion for parenteral administration is prepared as follows:

1. An aqueous phase is prepared from glycerol and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, lecithin, and clopidogrel free base in a vessel. The mixture is stirred at a temperature of approximately 60° C. until all ingredients are dissolved.
4. The oil mixture is gradually added to the aqueous phase under high shear mixing.
5. This mixture is then mixed with a high shear mixer (Polytron PT3100) at 10,000 rpm for 5 minutes to obtain a coarse emulsion. The emulsion pH is adjusted to 9-10.
6. The mixture is then homogenized with a high pressure homogenizer (APV 2000) at 10,000 psi for 10 cycles. The product temperature is controlled at ~45 degree C.
7. The resultant oil-in-water emulsion is cooled, pH adjust to 9-10 if necessary, and then transferred into a filling vessel.
8. The emulsion is then filtered with 0.45 micron filter and filled into containers under nitrogen and autoclaved at 121 C for 20 minutes.
9. The final pH is ~8.

Example 5. Preparation of Emulsion Using Clopidogrel Free Base Obtained as is from the Supplier by Aseptic Process Preparation of Emulsion Using Clopidogrel Free Base Obtained as is from the Supplier

| Formula | Quantities: g |
| --- | --- |
| Clopidogrel free base | 3.0 |
| soy bean oil | 10.0 |
| egg lecithin | 1.8 |
| glycerol | 2.25 |
| Vitamin E | 0.06 |
| sodium hydroxide | q.s. to pH 8-10 |
| Water for Injections | to 100 g |

All processing stages are carried out under nitrogen.

A sterile aqueous oil-in-water emulsion for parenteral administration is prepared as follows:
1. An aqueous phase is prepared from glycerol and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, lecithin, and clopidogrel free base in a vessel. The mixture is stirred at a temperature of approximately 60° C. until all ingredients are dissolved.
4. The oil phase is then added to the aqueous phase.
5. This mixture is then mixed with a high shear mixer (Polytron PT3100) at 10,000 rpm for 5 minutes to obtain a coarse emulsion. The emulsion pH is adjusted to 9-10.
6. The mixture is then homogenized with a high pressure homogenizer (APV 2000) at 10,000 psi for 10 cycles. The product temperature is controlled at ~45 degree C.
7. The resultant oil-in-water emulsion is cooled, pH adjust to 8-10 if necessary, and then transferred into a filling vessel.
8. The emulsion is then filtered with 0.45 micron filter and filled into containers under nitrogen.
9. The final pH is ~8.

Example 6. Preparation of Emulsion Using Clopidogrel Free Base Obtained as is from the Supplier by Aseptic Process Preparation of Emulsion Using Clopidogrel Free Base Obtained as is from the Supplier

| Formula | Quantities: g |
| --- | --- |
| Clopidogrel free base | 3.0 |
| soy bean oil | 10.0 |
| egg lecithin | 1.2 |
| glycerol | 2.25 |
| sodium hydroxide | q.s. to pH 8-10 |
| Water for Injections | to 100 g |

All processing stages are carried out under nitrogen.

A sterile aqueous oil-in-water emulsion for parenteral administration is prepared as follows:
1. An aqueous phase is prepared from glycerol and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, lecithin, and clopidogrel free base in a vessel. The mixture is stirred at a temperature of approximately 60° C. until all ingredients are dissolved.
4. The oil phase is then added to the aqueous phase under high shear mixing.
5. This mixture is then mixed with a high shear mixer (Polytron PT3100) at 6,000 rpm for 5 minutes to obtain a coarse emulsion. The emulsion pH is adjusted to 9-10.
6. The mixture is then homogenized with a high pressure homogenizer (APV 2000) at 10,000 psi for 10 cycles. The product temperature is controlled at ~45 degree C.
7. The resultant oil-in-water emulsion is cooled, pH adjust to 8-10 if necessary, and then transferred into a filling vessel.
8. The emulsion is then filtered with 0.45 micron filter and filled into containers under nitrogen.
9. The final pH is ~8.

Example 7. Preparation of Emulsion Using Clopidogrel Free Base and Lecithin as Surfactant and Oleic Acid as Co-Surfactant

| Formula | Quantities: g |
| --- | --- |
| Clopidogrel free base | 0.2 |
| soy bean oil | 10.0 |
| egg lecithin | 1.2 |
| Oleic acid | 0.03 |
| glycerol | 2.25 |

-continued

| Formula | Quantities: g |
|---|---|
| sodium hydroxide | q.s. to pH 9-10 |
| Water for Injections | to 100 |

All processing stages are carried out under nitrogen.

A sterile aqueous oil-in-water emulsion for parenteral administration is prepared as follows:

1. An aqueous phase is prepared from glycerol, egg lecithin, and Water for Injections. The pH of the aqueous phase is adjusted to ~9-10 with 1 N sodium hydroxide solution. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, oleic acid, and clopidogrel free base in a vessel. The mixture is stirred at a temperature of approximately 60° C. until all ingredients are dissolved.
4. The oil mixture is added to the aqueous phase under high shear mixing.
5. This mixture is then mixed with a high speed mixer (Polytron 3100) at ~10,000 rpm for 5 minutes to obtain a coarse emulsion.
6. The mixture is then sonicated with an ultrasonic processor (Fisher Scientific Sonic Dismembrator, Model 500) with for 30 minutes. The product temperature is controlled at ~45 degree C.
7. The resultant oil-in-water emulsion is cooled, pH adjust to 9-10, and then transferred into a filling vessel.
8. The emulsion is then filtered and filled into containers under nitrogen and autoclaved at 121 C for 20 minutes.
9. The final pH is ~8.

Example 8. Preparation of Emulsion with Clopidogrel Biosulfate (Comparative Example)

| Formula | Quantities: g |
|---|---|
| Clopidogrel bisulfate | 0.26 (equivalent to 0.2 g of free base) |
| soy bean oil | 10.0 |
| egg lecithin | 1.2 |
| glycerol | 2.25 |
| sodium hydroxide | q.s. to pH 9-10 |
| Water for Injections | to 100 g |

Follow the procedure described in Example 2 without autoclave. The final pH is ~7.4

Example 9. Preparation of Emulsion Using Clopidogrel Free Base

| Formula | Quantities: g |
|---|---|
| Clopidogrel free base | 2.0 |
| soy bean oil | 10.0 |
| egg lecithin | 1.2 |
| glycerol | 2.25 |

-continued

| Formula | Quantities: g |
|---|---|
| sodium hydroxide | q.s. to pH 9-10 |
| Water for Injections | to 100 |

Follow the procedure described in Example 2. The final pH is ~8.

Example 10. Preparation of Emulsion Using Premix of Clopidogrel Free Base in Soy Bean Oil Obtained by Conversion of Clopidogrel Bisulfate Salt to Free Base and Separation of the Sulfate Ion from the Free Base Prior to Manufacturing

| Formula | Quantities: g |
|---|---|
| Premix of clopidogrel free base in soy bean oil | Equivalent to 0.20 g of free base |
| soy bean oil | QS ad. 10.0 |
| egg lecithin | 1.2 |
| glycerol | 2.25 |
| sodium hydroxide | q.s. to pH 9-10 |
| Water for Injections | to 100 g |

All processing stages are carried out under nitrogen.

Preparation of Premix of Clopidogrel Free Base in Soy Bean Oil

1. Dissolve clopidogrel bisulfate salt in sufficient amount of water. Under continuous stirring, disperse required amount of soy bean oil into the aqueous solution and add 1 N sodium hydroxide by droplet wise to the mixture until the pH of the aqueous phase is 6.5 and above. Separate the oil phase containing the free base from the aqueous phase containing the sulfate and sodium ions, and wash the oil phase with water if necessary.

A sterile aqueous oil-in-water emulsion for parenteral administration is prepared as follows:

1. The drug-oil pre-mixture is heated under stirring to a temperature of approximately 60° C. Then, the oil phase is passed through a 0.22 micron filter and charged to a mixing vessel.
2. An aqueous phase is prepared from glycerol, egg lecithin, and water for Injections. The pH of the aqueous phase is adjusted to ~9-10 with 1 N sodium hydroxide solution. This mixture is stirred and heated to a temperature of approximately 60° C.
3. The aqueous phase is passed through a 0.22 micron filter and charged to a mixing vessel.
4. The oil mixture is added to the aqueous phase under high shear mixing.
5. The mixture is then mixed with a high shear mixer (Polytron PT3000) at ~10,000 rpm for 5 minutes to obtain a coarse emulsion.
6. The mixture is then circulated through a high pressure homogeniser at 10,000 psi for 5 cycles. The product temperature is controlled at ~45 degree C.
7. The resultant oil-in-water emulsion is cooled, pH adjust to ~9-10, and then transferred into a filling vessel.

8. The emulsion is then filtered with 0.45 micron filter and filled into containers under nitrogen and autoclaved at 121 C for 20 minutes.
9. The final pH is ~8.

Example 11. Preparation of Emulsion Using Clopidogrel Free Base

| Formula 2 | Quantities: g |
|---|---|
| clopidogrel free base | 0.20 g |
| soy bean oil | 10.0 g |
| egg lecithin | 1.8 |
| glycerol | 2.25 |
| Vitamin E | 0.06 |
| sodium hydroxide | q.s. to pH 9-10 |
| Water for Injections | to 100 g |

Follow the procedure described in Example 3. The final pH is ~8.

Example 12. Preparation of Emulsion Using Clopidogrel Free Base

| Formula 2 | Quantities: g |
|---|---|
| clopidogrel free base | 2.8 g |
| soy bean oil | 0.17 g |
| egg lecithin | 0.54 |
| glycerol | 2.25 |
| sodium hydroxide | q.s. to pH 9-10 |
| Water for Injections | to 100 g |

Follow the procedure described in Example 3. The final pH is ~8.

Example 13. Characterization of Emulsion Droplet Size Distribution by NanoZeta Sizer: Comparison Emulsions Made with Clopidogrel Free Base and Bisulfate Salt The emulsion obtained from Example 8 and 10 were tested for particle size distribution. Malvern Zetasizer Nano-ZS ZEN3600 was used to measure the emulsion droplet size distribution. FIG. 1 shows the mean droplet size (intensity-average, nm) of the emulsions prepared with clopidogrel free base (Example 10) and clopidogrel bisulfate (Example 8). The emulsion using free base is stable upon autoclave, freeze thaw and storage under refrigeration for 1 year, whereas the emulsion using clopidogrel bisulfate showed dramatic change in particle size after autoclave and freeze thaw.

Example 14. Comparison Chemical Stability Between Emulsion of Current Invention and SB-E-CD and HP-B-CD Complex HPLC Method
A chiral LC method was used for impurity testing and enantiospecific assay. As stationary phase, an ULTRON ES-OVM column, 5 um (4.6 mm×150 mm i.d.) was used. The mobile phase consisted of Mobile Phases: A, 1.36 g Sodium Phosphate monobasic (NaH2PO4.H2O) in 1.0 L purified water; B, acetonitrile. Binary gradient with constant flow rate of 1.0 mL/min and 18 minute total run time. The injection volume 5-10 µl and UV detection was performed at 220 nm.

Figure 2:
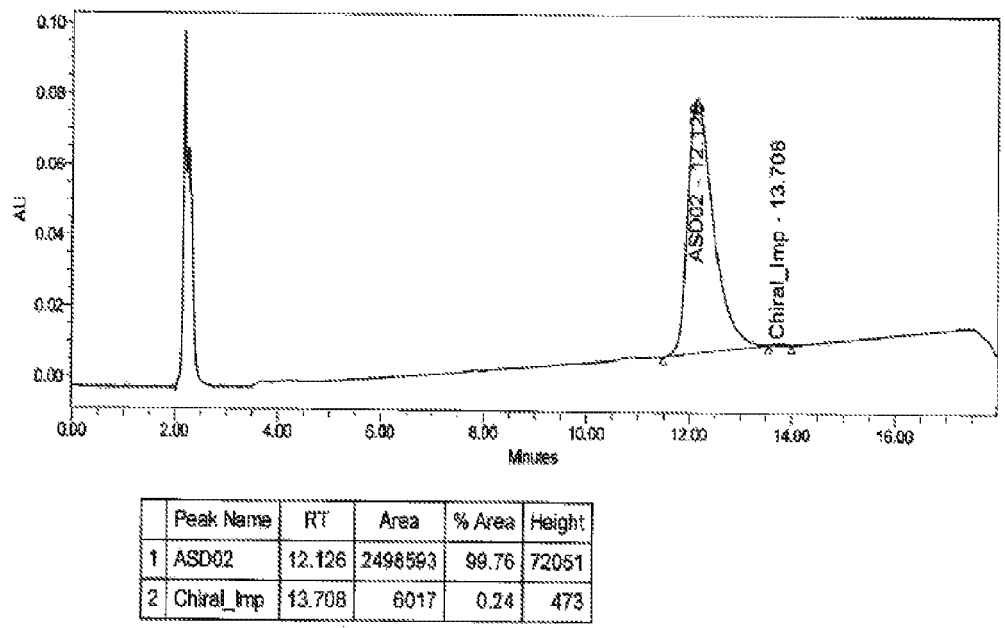
FIG. 2 HPLC Chromatogram of emulsion of clopidogrel free base after storage under refrigeration (at ~5° C.) for 1 year (Example 10).

The major degradation impurities for clopidogrel emulsion of this invention were found to be impurity C (Chiral R). The hydrolytic degradation impurity A was the minor degradant (<1.2%) for the emulsion product, and no significant change in the Impurity A was observed. Therefore, the chemical stability of the emulsion product of this invention was monitored with Impurity C (FIG. 2). The stability data (FIGS. 3 and 4) of emulsion using free base showed better stability than cyclodextrin-based clopidogrel solution.

Figure 3:
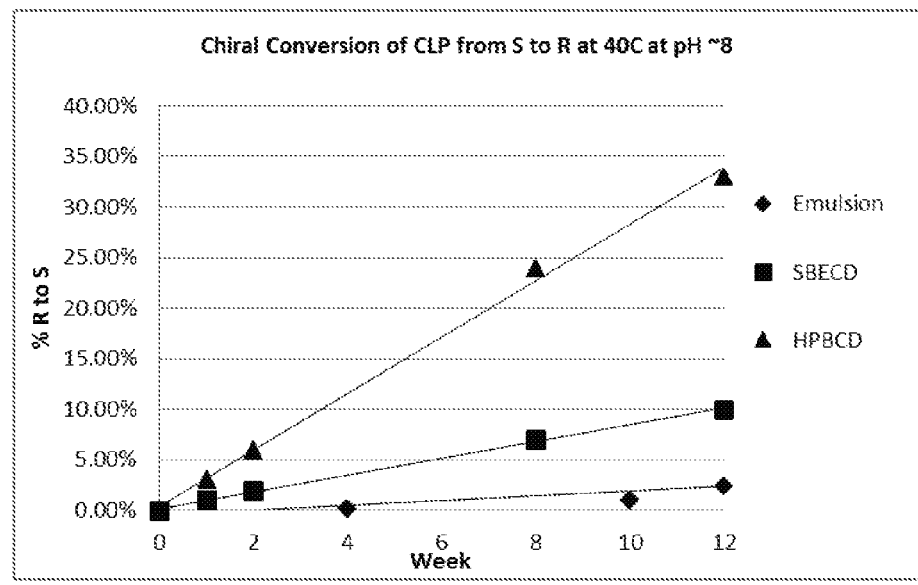
FIG. 3 shows comparison of percentage of clopidogrel chiral conversation from S to R stored at 40 degree Celsius between the clopidogrel emulsion of this invention (Example 10) vs clopidogrel-HPBCD and SBECD complex at pH of approximately 8.

FIG. 3 shows comparison of percentage of clopidogrel chiral conversation from S to R stored at 40 degree Celsius between the clopidogrel emulsion of this invention (Example 10) vs clopidogrel-HPBCD and SBECD complex at pH of approximately 8 (literature value from US20100292268).

Figure 4:
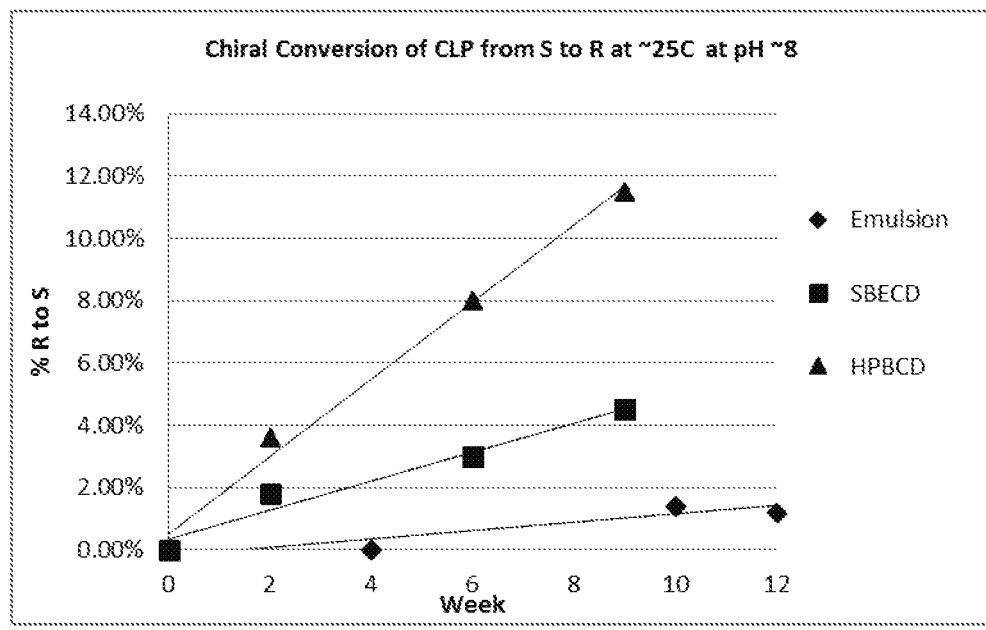
FIG. 4 shows comparison of percentage of clopidogrel chiral conversation form S to R when stored at 25 degree Celsius between the clopidogrel emulsion of this invention (Example 10) vs clopidogrel-HPBCD and SBECD complex at pH of approximately 8.

FIG. 4 shows comparison of percentage of clopidogrel chiral conversation form S to R when stored at 25 degree Celsius between the clopidogrel emulsion of this invention (Example 10) vs clopidogrel-HPBCD and SBECD complex at pH of approximately 8 (literature value from US20100292268).

Example 15. Comparison of Emulsions Chemical Stability Made with Clopidogrel Free Base (Example 10) and Bisulfate Salt (Example 8)

HPLC Method described in Example 14 was followed.

The stability data (FIG. 5) of emulsion using clopidogrel free base showed better stability than the one prepared with clopidogrel sulfate salt.

Figure 5:
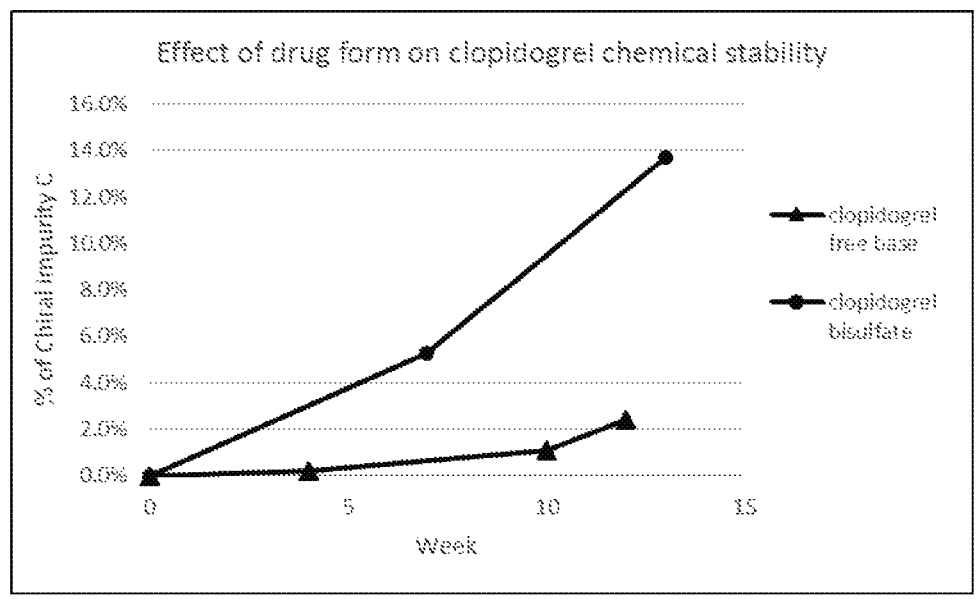
FIG. 5 shows comparison of percentage of clopidogrel chiral conversation form S to R when stored at 40 degree Celsius between emulsion prepared using clopidogrel free base (Example 10) vs emulsion prepared with clopidogrel bisulfate salt (Example 8).
Figure 6:
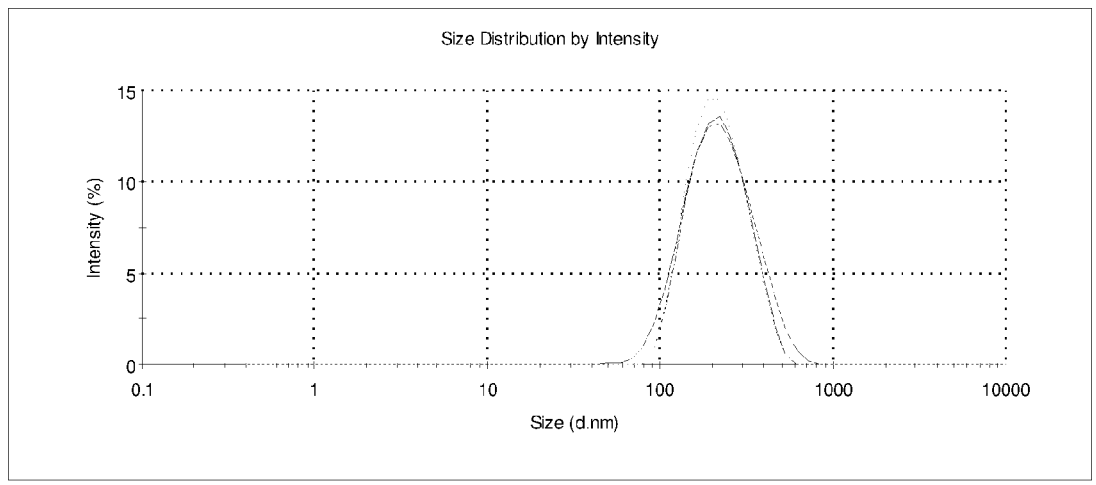
FIG. 6. Overlay of emulsion (Example 6) droplet size distribution for freshly prepared emulsion sample, emulsion sample after 19 weeks storage at room temperature, and emulsion sample after 19 weeks storage at 40° C.

FIG. 5 shows comparison of percentage of clopidogrel chiral conversation form S to R when stored at 40 degree Celsius between emulsion prepared using free base (Example 10) vs emulsion prepared with clopidogrel sulfate salt (Example 8).

Example 16. Stability Summary of Emulsion of Example 10

Stability data in Table 2 below shows that the emulsion of example 10 is stable at least for 52 weeks when stored under refrigeration.

TABLE 2

Stability summary of Emulsion Example 10

| | Stability conditions (~5° C.) | | | | |
|---|---|---|---|---|---|
| Weeks | 0 | 12 | 14 | 20 | 52 |
| Impurity C | 0 | 0.56% | 0.50% | 1.04% | 0.24% |
| Droplet size(d50), nm | 198.4 | NT | NT | NT | 198.1 |
| pH | 8.10 | NT | NT | NT | 6.18 |

Example 17. Stability Summary of Emulsion of Example 6

Stability data in Tables 3 and 4 below shows that the emulsion of example 6 is stable at least for 19 weeks when stored under refrigeration (~5° C.) or room temperature (~25° C.).

TABLE 3

Stability summary of Example 6

| | Stability conditions at ~25° C. | |
|---|---|---|
| weeks | 0 | 19 |
| Impurity C | 0.10% | 0.90% |
| Droplet size (D50), nm | 191.7 | 207.6 |
| pH | 7.8 | 6.6 |

TABLE 4

Stability summary of Example 6
Stability conditions at ~5° C.

| weeks | 0 | 19 |
|---|---|---|
| Impurity C | 0.10% | 0.14% |
| Droplet size (D50), nm | 192.0 | 193.0 |
| pH | 7.8 | 6.7 |

What is claimed is:

1. An oil-in-water emulsion comprising:
clopidogrel free base encapsulated in an oil phase of the oil-in-water emulsion; a surfactant and an optional co-surfactant;
a water phase being substantially free of the clopidogrel free base; a pH adjustment agent;
wherein the clopidogrel free base comprises about 0.01% to about 10% (w/v) of the composition;
wherein a mean droplet size of the emulsion is 100 nm to 500 nm; and
wherein the clopidogrel free base maintains an overall purity of at least 97.5% for at least six months.

2. The emulsion of claim 1 further comprising one or more agents selected from the group consisting of a chelating agent, an osmotic agent, a preservative, a suspending agent, and a buffering agent.

3. The emulsion of claim 1 wherein the composition contains less than or equal to 1.2% of impurity A of the clopidogrel free base and less than or equal to 1.5% of impurity C of the clopidogrel free base.

4. The emulsion of claim 1 wherein the pH of the emulsion is greater than 5.5.

5. The emulsion of claim 1 wherein the oil phase comprises about 10% to about 20% (w/v) of the composition.

6. The emulsion of claim 1 wherein the oil phase is selected from one or more pharmaceutical-grade oils consisting of medium chain triglycerides, soy bean oil, safflower seed oil, olive oil, cottonseed oil, sunflower oil, fish oil, castor oil, sesame oil, peanut oil, and corn oil.

7. The emulsion of claim 1 wherein the total weight of the surfactant and the optional co-surfactant is about 0.5% to about 6% (w/v) of the composition.

8. The emulsion of claim 7 wherein the emulsion comprises about 0.6% to about 2.4% (w/v) of surfactant and 0.0% to about 0.5% (w/v) of the optional co-surfactant, wherein the surfactant is egg lecithin and the co-surfactant is oleic acid or sodium oleic.

9. The emulsion of claim 1 wherein the composition comprises about 0.15% to about 3% (w/v) of clopidogrel free base, about 10% to about 20% (w/v) of soybean oil, about 1.2% to about 1.8% (w/v) of egg lecithin, about 2.25% (w/v) of glycerol, sodium hydroxide, and water.

10. An oil-in-water emulsion comprising:
clopidogrel free base encapsulated in an oil phase of the oil-in-water emulsion;
a surfactant and an optional co-surfactant;
a water phase being substantially free of the clopidogrel free base;
a pH adjustment agent;
wherein the clopidogrel free base comprises about 0.01% to about 10% (w/v) of the composition;
wherein a mean droplet size of the emulsion is 100 nm to 500 nm; and
wherein the composition contains less than or equal to about 1.2% of impurity A of the clopidogrel free base and less than or equal to 1.5% of impurity C of the clopidogrel free base.

11. The emulsion of claim 10 wherein the oil phase comprises about 1% to about 30% (w/v) of the composition.

12. The emulsion of claim 10 wherein the emulsion comprises about 0.15% to about 10% (w/v) of the clopidogrel free base.

13. An oil-in-water emulsion comprising:
clopidogrel free base encapsulated in an oil phase of the oil-in-water emulsion;
a surfactant and an optional co-surfactant,
wherein the surfactant and the optional co-surfactant comprise about 0.5% to about 6% of the emulsion;
a water phase being substantially free of the clopidogrel free base;
a pH adjustment agent;
wherein the clopidogrel free base comprises about 0.15% to about 10% (w/v) of the composition;
wherein the clopidogrel free base maintains an overall purity of at least 97.5% for at least six months;
wherein the composition contains less than or equal to 1.2% of impurity A of the clopidogrel free base and less than or equal to 1.5% of impurity C of the clopidogrel free base; and
wherein a mean droplet size of the emulsion is 100 nm to 500 nm.

14. The emulsion of claim 13 wherein the emulsion comprises about 0.16% to about 3% (w/v) of the clopidogrel free base.

15. The emulsion of claim 13 wherein a mean droplet size of the emulsion is about 100 nm to about 300 nm.

16. The emulsion of claim 13 wherein the pH adjustment agent is a buffer or sodium hydroxide.

17. The emulsion of claim 13 wherein the pH adjustment agent adjusts the pH of the emulsion to about 6.5 to about 9.0.

18. The emulsion of claim 13 wherein the water phase is present in about 70% to about 90% (w/v).

* * * * *